United States Patent
Lee

(10) Patent No.: US 8,025,657 B2
(45) Date of Patent: Sep. 27, 2011

(54) CLOSED LOOP FAT TRANSPLANTATION SYSTEM

(76) Inventor: Hee-Young Lee, Kunsan (KR)

( * ) Notice: Subject to any disclaimer, the term of this patent is extended or adjusted under 35 U.S.C. 154(b) by 208 days.

(21) Appl. No.: 10/543,269

(22) PCT Filed: Jan. 20, 2004

(86) PCT No.: PCT/KR2004/000123
§ 371 (c)(1), (2), (4) Date: Mar. 14, 2006

(87) PCT Pub. No.: WO2004/067065
PCT Pub. Date: Aug. 12, 2004

(65) Prior Publication Data
US 2006/0224144 A1 Oct. 5, 2006

(30) Foreign Application Priority Data
Jan. 25, 2003 (KR) .................. 10-2003-0005029

(51) Int. Cl.
*A61M 1/00* (2006.01)
(52) U.S. Cl. .................. 604/542; 604/540; 604/35
(58) Field of Classification Search ............ 600/562; 604/542, 540, 27, 35, 218
See application file for complete search history.

(56) References Cited

U.S. PATENT DOCUMENTS

| | | | | |
|---|---|---|---|---|
| 3,517,668 A | * | 6/1970 | Brickson | 604/209 |
| 3,775,849 A | * | 12/1973 | Condon | 433/87 |
| 5,180,371 A | * | 1/1993 | Spinello | 604/118 |
| 5,238,003 A | * | 8/1993 | Baidwan et al. | 600/578 |
| 5,685,864 A | * | 11/1997 | Shanley et al. | 604/211 |
| 5,865,803 A | * | 2/1999 | Major | 604/122 |
| 5,887,764 A | * | 3/1999 | Ennis et al. | 222/389 |
| 6,123,687 A | * | 9/2000 | Simonyi et al. | 604/207 |
| 6,234,994 B1 | * | 5/2001 | Zinger | 604/82 |
| 6,258,054 B1 | * | 7/2001 | Mozsary et al. | 604/22 |
| 6,537,246 B1 | * | 3/2003 | Unger et al. | 604/82 |
| 2001/0047183 A1 | * | 11/2001 | Privitera et al. | 606/170 |
| 2002/0022854 A1 | * | 2/2002 | Irion et al. | 606/171 |
| 2002/0077601 A1 | * | 6/2002 | Kawagishi et al. | 604/224 |
| 2002/0115933 A1 | * | 8/2002 | Duchon et al. | 600/432 |
| 2003/0158513 A1 | * | 8/2003 | Brannon et al. | 604/35 |

FOREIGN PATENT DOCUMENTS

| | | | |
|---|---|---|---|
| FR | 2627087 A | * | 8/1989 |
| JP | 62-72647 | | 5/1987 |
| JP | 03-188844 | | 8/1991 |
| JP | 04-322658 | | 11/1992 |

(Continued)

*Primary Examiner* — Max Hindenburg
*Assistant Examiner* — Michael C Stout
(74) *Attorney, Agent, or Firm* — Ladas & Parry LLP

(57) ABSTRACT

The present invention provides a closed loop fat transplantation system newly designed to aspirate a fat, to handle it without receptacle transfer and to transplant it into the human body, which is composed of a fat transplantation receptacle (hereinafter referred as FT receptacle) and an exterior mechanical pressurization and decompression means. The said FT receptacle includes a vertical hem portion where joining selectively individual syringe needle or cannelae, a cylinder-shaped receptacle into front fat storing space and rear pressurization and decompression space. The said pressurization and decompression means can give positive/negative pressure to the fat storing space through the piston head of the said FT receptacle and it has a structure separable from the said FT receptacle. Accordingly, fat transplantation can be performed without receptacle transfer using the same FT receptacle extracting fat from patient's body giving negative pressure through the piston head to the fat storing space.

1 Claim, 6 Drawing Sheets

FOREIGN PATENT DOCUMENTS

| | | |
|---|---|---|
| JP | 10-500030 | 1/1998 |
| JP | 2001-070444 | 3/2001 |
| JP | 2002-126083 | 5/2002 |
| JP | 2002126083 A * | 5/2002 |

* cited by examiner

CLOSED LOOP FAT TRANSPLANTATION SYSTEM

TECHNICAL FIELD

The present invention relates to a closed loop fat transplantation system, which is used when aspirating patients' fat and transplanting it into his other sites again, more particularly, the present invention comprises steps of extracting a fat from patient using a syringe-structural bidirectional receptacle which can use mechanical negative/positive pressure in the same space, disposing of the aspirated fat without receptacle transfer, transplanting it into the interior of the body.

BACKGROUND ART

Various kinds of fat aspiration and fat transplantation have been already performed, but fat transplantation has a problem that its application range is little due to many limitations.

The process of conventional fat transplantation is as follows. The region of patient's body was small incised. A pipe (cannulae) having a hole on its distal end was inserted. Fat was aspirated through the cannulae using negative pressure. Liquid ingredients such as a serum, blood, injections in the extracted fat were removed except fat. The fat was bottled in a syringe and injected by manually through a thin needle.

When extracting a fat for transplantation, method of making negative pressure is classified into either use of machine or syringe.

In case of using machine for making negative pressure, the cannulae was equipped with a filter in its middle portion to strain fat. The fat was transferred and bottled into a syringe then injected.

Problems on this occasion are

1) Unless a large filter is used, fine hole of the filter gets to be clogged easily. Therefore generally suitable size of filters would be used as allowing for some fat loss, accordingly fat and other fine tissues were lost.

2) In the process of fat transfer from filter to syringe, the process became complicated and much time was required. Consequently the frequency of air contact becomes increased, so that the possibility of contamination gets high.

3) Also loss of a plenty amount of fat is caused because much amount of tissue stuck to this path.

4) It takes much time and it is inconvenient since hand-operated pressure is used during injection.

Meanwhile, in case of using a syringe and hand-operated negative pressure, the syringe equipped with cannulae was injected into the human body at the maximum forward position of its piston. As the piston was pulled backward by manually, negative pressure was formed in space in front of the syringe piston. At this condition, user locked the piston.

Fat was aspirated while the syringe was reciprocated. Once the syringe was filled with the fat to some degree, the fat would be transferred to other places or a syringe for centrifuge/injection.

Extracted fat was transferred to a syringe for injection then transplanted. In order to use hand-operated injection, the piston syringe having a thick diameter can't be utilized such as a syringe for aspiration due to its big resistance when the fat passes through the needle.

Problems at this situation are

1) Negative pressure drops suddenly due to small amount of air flowing in the syringe at the very moment or just vapor pressure when piston is pulled and locked to form negative pressure. Therefore there is an inconvenience of releasing the lock and repeating again the process.

Efficiency of maintaining a negative pressure by only space of 50-60 cc is extremely low in comparison with the negative pressure formed by machine through air movement of thousands cc per 1 second.

Also the process is hard and troublesome to lock the piston of syringe as pulling it.

2) User has to transfer the aspirated fat to the syringe for centrifuge/injection, so that this process is also complicated and it requires a lot of time. At this time the fat gets to come into contact with a great quantity of air in several spaces, therefore the possibility of contamination is increased.

3) It takes much time and it is inconvenient since hand-operated pressure is used at the time of injection.

The said methods stand on the basis of hand-operated or mechanical method from the viewpoint of fat extraction, on the other hand transplantation of aspirated fat has been dependent upon entirely hand-operated injection method, accordingly some problems are indicated as following.

1) A problem is generated due to low injection pressure.

Pressure for fat movement through syringe needle is very large.

On this account, even though syringe for only fat injection utilizing the leverage is used, user must repeat the process to transplant 100 cc of fat dozens of times.

Therefore it takes much time, user suffers inconvenience. Besides jet pressure is also low. If the resistance at recipient site is strong, injection can't be performed, fat gets together in the place of weak resistance after all.

Thereby it causes following. First, desired cosmetic effect can't be displayed. Second, in case of fat gathered in one place and not spread out evenly, the contacting area with recipient site becomes small in comparison with same amount of fat. Lastly, survival rate is rapidly decreased in view of transplantation characteristic because the transplant gets to be alive with nutrition by contact before blood vessel has been formed with the passage of time.

Under the low survival rate, such as volume decrease, necrosis of middle site away from the contacting site, infection of necrosis tissues are discussed. Since they can be diverted into fatal infection symptoms all over the body, mass transplantation beyond regular amount (about 100 cc or more) is difficult and actually it has been hardly carried.

2) Another serious problem is infection. As the necrosis tissues become a good culture media, infection can spread in a flash. Although the fat tissue is not a necrosis, once it is separated from the body, its resistibility against germs gets extremely weak. Therefore it is unendurable against some germs, it can be spread into infection.

Infection appears when generally the number in the regular amount of tissue is more than a certain level. Even a germ exists in the air, the more the contacting time with non-sterilized indoor air and contacting areas, the higher the possibility of infection.

Lately a method using a suction receptacle itself as an injection receptacle is attempted, it can reduce occasion of indoor air contact and possibility of contamination from other receptacle. However it isn't suitable in case of mass fat transplantation such as over 100 cc of lipoinjection to one site since it uses small syringes.

At present, fat transplantation is used for treating wrinkles and small depression, but mass fat transplantation enough to breast augmentation is scarcely used due to infection and low survival rate.

Although it is carried out, it is considered as impracticable since it takes a lot of time and force.

3) Hand-operated injection method can't regulate injection pressure.

Since excessive high injection pressure affects not only adipose survival rate but also fat embolism, it is necessary to regulate precisely. In the process of fat entrance, resistance is generated. If the resistance can't be perceived, injection circumstance is invisible, so that equal distribution can't be accomplished at each part.

DISCLOSURE OF THE INVENTION

The present invention is for the purpose of overcoming limitation of such conventional fat transplantation method.

Namely, the object of the present invention is to provide a fat transplantation system, which solves the problems of mass fat transplantation such as inefficiency due to a lot of absorption, possibility of serious side effects like an infection, a lot of surgery time. Thereby it makes impossible mass fat transplantation possible and secure, also maximizes convenience of surgery.

In accordance with the present invention, the object can be accomplished by the provision of a new idea of a receptacle for injection-transplantation and fat transplantation system, whose structure can give negative/positive pressure to the said receptacle by means of mechanical method.

Furthermore, the object of the present invention is to provide a fat transplantation system to use existing syringes in order to utilize the existing system simply and economically, to organize an apparatus in order to use air pressure itself which was dumped from suction vacuum pump, to utilize the most convenient means in accordance with liposuction position and transplantation amount, to utilize properly an observation/monitoring device, a check valve preventing air inflow, another check valve removing air in order to protect serious side effect like fat embolism, to minimize infection problem.

For the object of the present invention, a new structural-receptacle for fat transplantation and closed loop fat transplantation system composed of said receptacle are provided.

According to the present invention, the receptacle has a structure as one for fat extraction as well as pressure receptacle for fat transplantation, which is composed of a structure giving positive/negative pressure by mechanical system to improve efficiency of liposuction and fat transplantation.

With the said fat transplantation receptacle, compositions of closed loop fat transplantation system according to the present invention are a handpiece improving efficiency of liposuction, a pressure pressurization and decompression means, a centrifuge and etc. These compositions are essentially required or functioning very usefully in all process of fat transplantation; extracting a fat, treating the extracted fat, removing liquid, transplanting the fat into the body.

As a basic structure, the said fat transplantation receptacle (hereinafter referred s FT receptacle) may comprise a vertical hem portion where joining selectively individual syringe needle or cannulae, a cylinder-shaped receptacle where the fat was aspirated and stored, a piston head parceling the said cylinder-shaped receptacle into front fat storing space and rear pressurization and decompression space, and it may be composed of various embodiments according to the object of the present invention.

Pressurization and decompression means can give positive/negative pressure to the fat storing space through the piston of the said FT receptacle, and it has a structure separable from the said FT receptacle.

The said pressurization and decompression means is applicable with various ways such as mechanical process using a rack, pinion gear or a pneumatic cylinder process or exterior suction/air pressure unit and etc.

Centrifuge is included as incidental equipment, which is included as useful composition during pure fat transplantation separating and removing liquid ingredients such as blood, injections from extracted fat.

Moreover, handpiece is included as a composition, which is used as valuable means improving efficiency of fat extraction giving fine oscillation to cannulae during liposuction.

Each of the said compositions can perform fat transplantation without receptacle transfer using the same FT receptacle by extracting fat from patient's body giving negative pressure through the piston head to the fat storing space, transplanting the fat into the patient's other sites giving positive pressure through that. Thereby it prevents fundamentally microbe infection by air contact during the process of fat extraction and transplantation, reduces troublesome to transfer and bottle the extracted fat during transplantation, makes mass fat transplantation possible without side effects.

BEST MODE FOR CARRYING OUT THE INVENTION

Now, preferred embodiments of the present invention will be described in detail with reference to the annexed drawings.

Figure 1:
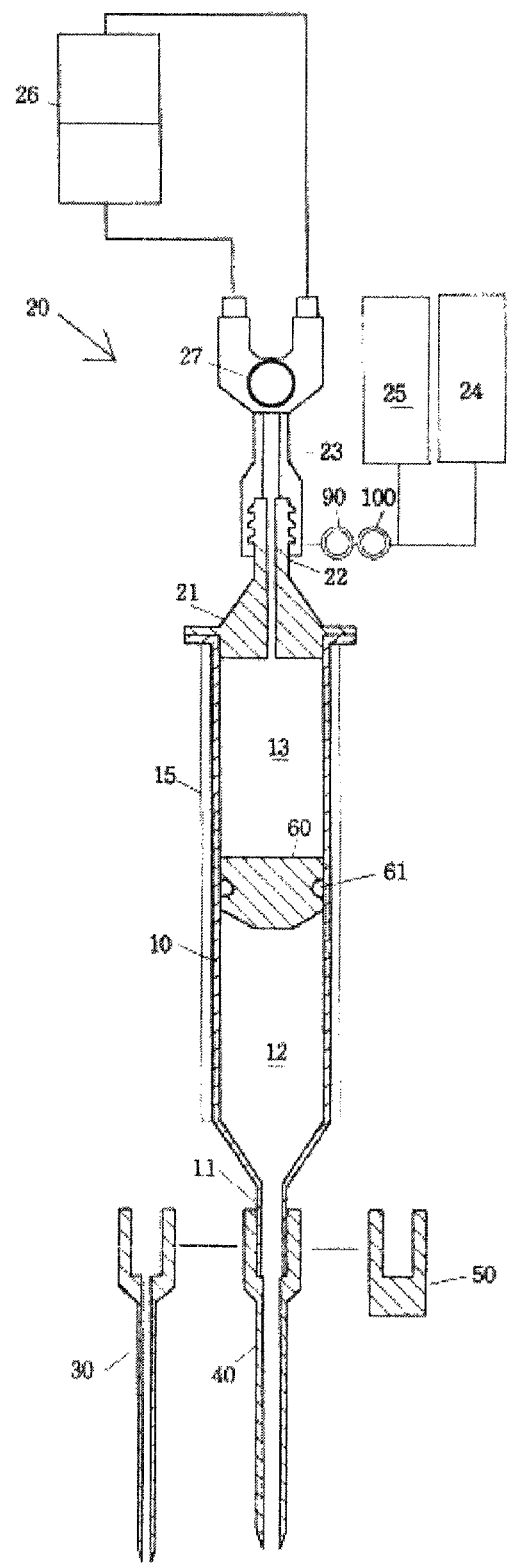
FIG. 1. schematic view according to the present invention

FIG. 1 illustrates a closed loop fat transplantation system in accordance with one embodiment of the present invention. The closed loop fat transplantation comprises a FT receptacle 10, a pressurization and decompression means 20 joined with each suction unit and air pressure unit.

According to the said embodiment, the FT receptacle is designed to a cylinder-shaped receptacle to attach selectively an independent syringe needle 30, a cannulae 40 or stopple 50 to its vertical hem portion 11.

Also, the said FT receptacle includes a piston head 60, which is inserted to parcel out the inside of the cylinder-shaped receptacle between front fat storing space 12 and rear pressurization and decompression space 13.

The FT receptacle has a shape similar to general disposable syringe, but it is designed for reinforce structure to operate high pressure on its inside. In case of using disposable syringe itself, a separate reinforcing case 15 is covered on it. O-ring 61 is worn the piston head 60 to improve airtight pressure.

The piston head 60 is a shape having no shaft, which is composed to give negative/positive pressure to its front space by the given pressure through its rear pressurization and decompression space.

As a pressurization and decompression means 20, a rear stopple 21 is joined to keep airtight the rear pressurization and decompression space of the FT receptacle, a connecting jack 22 is formed on the said rear stopple to join with a external tube 23, therefore the pressurization and decompression means has a structure connected with exterior suction unit 24 or air pressure unit 25.

The said exterior suction unit 24 or air pressure unit 25 is used as an independent pressurization and decompression means, which has a structure to select decompression and pressurization through a value 27 using one vacuum pump 26 like the embodiment according to FIG. 1.

Figure 2:
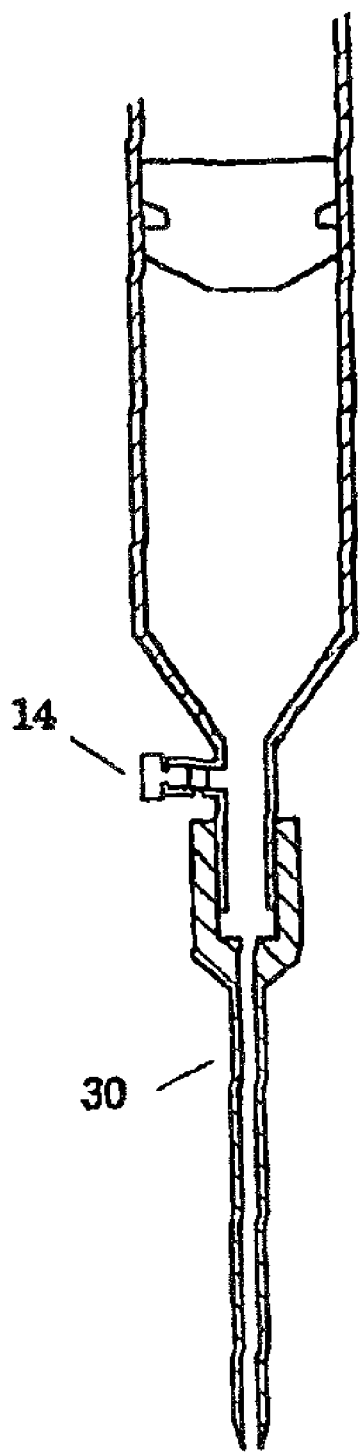
FIG. 2. schematic view of check valve mounted according to one embodiment of the present invention FIG. 3. schematic view of centrifuge included according to alternative embodiment of the present invention FIG. 4. schematic view of composing of powered handpiece according to further embodiment of the present invention FIG. 5. schematic view of mechanical means for pressurization and decompression according to further embodiment of the present invention.

FIG. 2 illustrates a one-way check valve 14 is formed on the said compositions of the present invention in accordance with alternative embodiment. To remove air in the FT receptacle, the one-way check valve is formed on the receptacle's vertical hem portion where the syringe needle or cannulae was joined selectively.

Preferably, the said check valve is a threaded type, thereby it will not open by negative/positive pressure during liposuction and injection after air removal.

Figure 3:
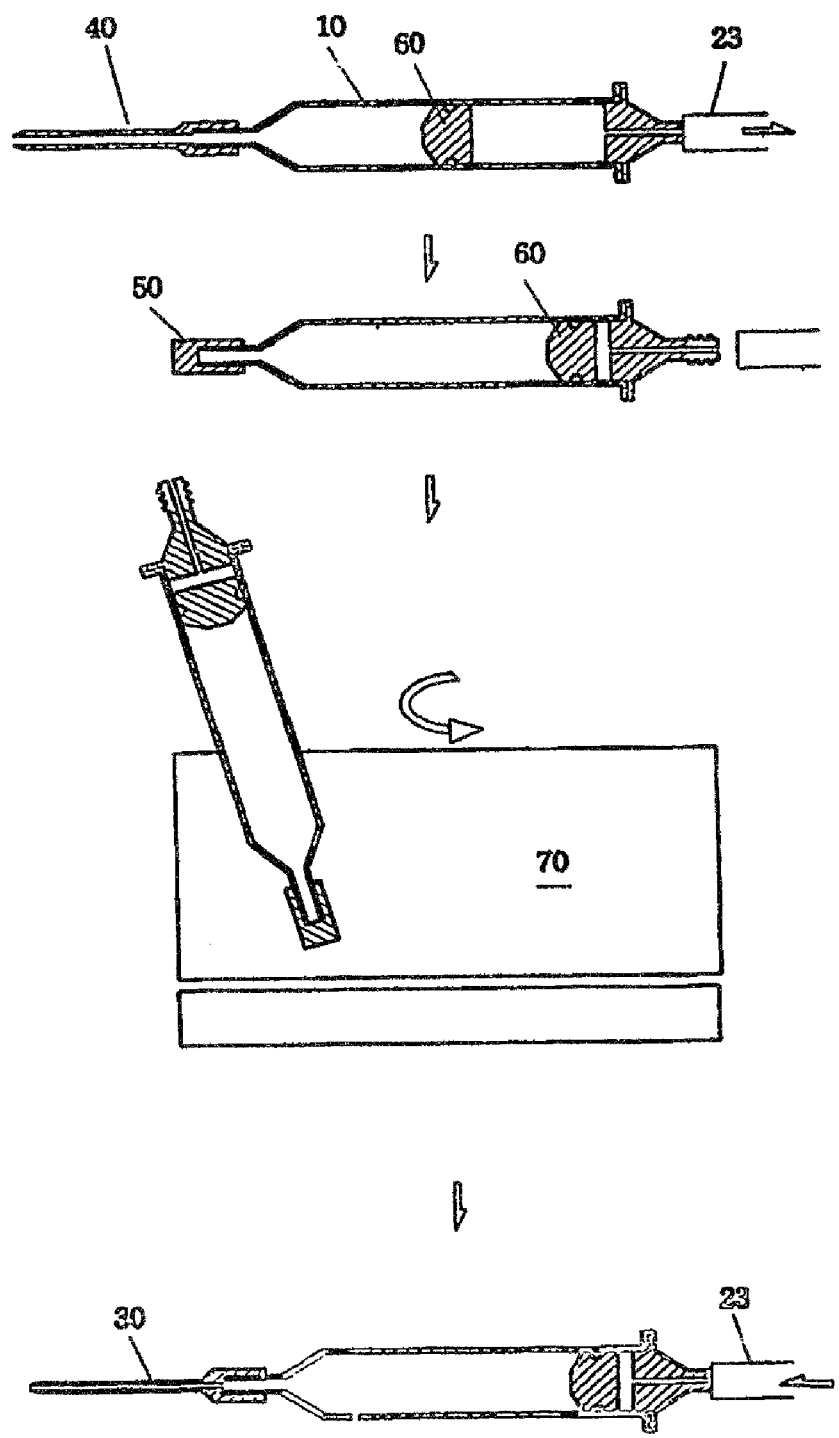

FIG. 3 illustrates the present invention including centrifuge in accordance with further embodiment, which comprises a stopple front 50 joined with the vertical hem portion of the FT receptacle, a centrifuge included as a system composition to remove the liquid ingredients from extracted fat then make the fat transplantable.

According to the said embodiment, the cannulae 40 was joined with the vertical hem portion, the piston head was located at its maximum forward position. After partial incision of liposuction site, the tip of the cannulae is inserted into the body.

At this condition, if negative pressure was made in the rear space of the piston by means of the rear stopple, the negative pressure was also made in the front space of that and fat was being aspirated and bottled in the receptacle while the piston moved back.

At this time, as long as the cannulae has been inserted in the body, the front of the receptacle functions as an airtight space. Therefore there is no chance of air contact.

The piston head as a free gearing would be located at the point that the both spaces have an equal pressure, and it has as moved back as the receptacle has being filled with fat.

After the receptacle was filled with the fat, the cannulae would be separated from the FT receptacle, the external tube 23 for rear pressurization and decompression would be separated from the connecting jack 22, and then the vertical hem portion is capped with a stopple 50.

Under that condition, the FT receptacle itself was mounted to centrifuge 70. If it is centrifuged, liquid ingredients of fat are separated.

At this time, after the front stopple was removed and the injection needle was attached to the vertical hem portion of the receptacle, external tube is joined again with rear connecting jack connected with an air pressure unit. If pressurizing a little, the liquid ingredients are removed.

Thereafter the syringe needle 30 is inserted into the donor site and pressurized, the fat is injected while the piston head moves forward.

If the air is generated during fat injection, the fat injection-transplantation is continued at the state of air exhaust opening a check valve 14.

When negative pressure is formed to aspirate fat, the cannulae has to be inserted into the body. When the cannulae is drawn, the liposuction has to be stopped in advance not to form the negative pressure and air inflow into the inside of the syringe must be intercepted. However, in case of air inflow by operator's mistake, he has to push out the air between the cannulae and FT receptacle pressurizing the piston head a little. Or he has to mount the FT receptacle to centrifuge upside down to separate the air, and remove the air as if removing the liquid, then perform the process for liquid separation.

If centrifugation for liquid separation is performed as a method of removing air, the air is collected over the fat layer. In this case, a long needle is inserted into the space containing air through the front tube and the piston head is pushed, the air can be exhausted.

The centrifuge is equipped with sterilizable adapter, which can fix the FT receptacle for contamination protection.

Figure 4:
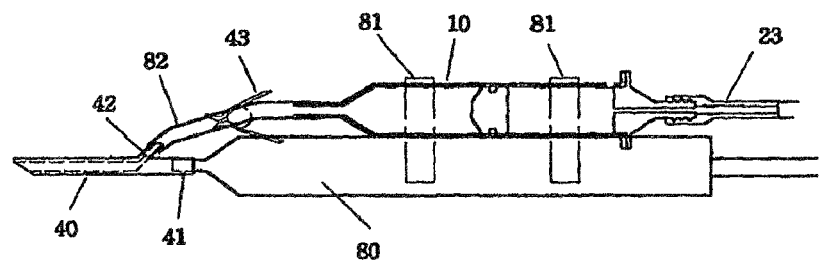

FIG. 4 illustrates the present invention including a reciprocating powered handpiece 80 in accordance with further embodiment, which comprises a powered handpiece 80 to perform the liposuction easily, a clip 81 to fix the FT receptacle to the said handpiece in the shape of detachable type, a silicone tube 82 to allow the FT receptacle aspirate the fat aspirated from the cannulae joined to vertical hem portion of reciprocating handpiece.

The handpiece gives an oscillation to cannulae by its oscillator reciprocating back and forth at about 1 cm of stroke, that is, it as a factor for easy liposuction is composed to attach the cannulae to its front.

The cannulae for the said structure is composed of a coupling socket 41 to be attached to the vertical hem of reciprocating handpiece, a silicone tube socket 42 continuing to the internal pipe. One tip of silicone tube is attached to the said silicone tube socket, another tip of that is attached to the vertical hem portion of the FT receptacle. By means of negative pressure on the FT receptacle, the FT receptacle is filled with the aspirated fat through the cannulae.

The clip joins the FT receptacle to the handpiece to allow user to handle easily during liposuction, and it fixes the handpiece to the FT receptacle to detach the FT receptacle conveniently during fat transplantation or centrifugation.

According to the said composition, fat is aspirated making negative pressure in the FT receptacle under the circumstances that the FT receptacle and the handpiece were joined each other; the cannulae were joined to the said handpiece.

It is desired that a hand-operated valve be joined to the said silicone tube in the shape of forceps in order to open and close the silicone tube at operator's convenience.

This kind of structure can minimize the possibility of air inflow by opening the valve under the only airtight circumstances, since the cannulae remains in the body.

If air flows early into the FT receptacle by mistake, it is possible to exhaust the air by standing the FT receptacle to move the air layer upward and giving a pressure to that slowly.

Once the FT receptacle was filled with fat, the handpiece is detached from it, and its vertical hem portion is capped with a stopple. Afterwards it is mounted to the centrifuge, then centrifuged.

If liquid ingredients gathered in the front space of FT receptacle, the stopple should be drawn and a syringe should be attached instead. Then the liquid ingredients are removed by giving a pressure to the piston head a little while the vertical hem portion of the FT receptacle faces downward.

Fat transplantation can be performed easily and conveniently by injecting fat into necessary site using air pressure. In case of mass fat transplantation like breast augmentation, small amount of fat can be injected evenly among tissues, so that fat embolism can be prevented.

The said example can adjust pressure at the appropriate value without difficulty since the rear stopple 21 was joined as pressurization and decompression means to make airtight the rear of the piston head, then the connecting jack was joined to the external tube previously connected with an air pressure unit or a suction unit.

In addition, the said example can be composed of a valve to regulate selectively air/suction pressure using a vacuum pump, more preferably, both a regulator 90 which can control the strength of pressurization and a speed regulator 100 which can control the flow velocity are formed on the pressure supply tube. Therefore it can be composed in order to monitor and regulate the injection speed/pressure, which are able to maintain regular values by signal feedback.

Figure 5:
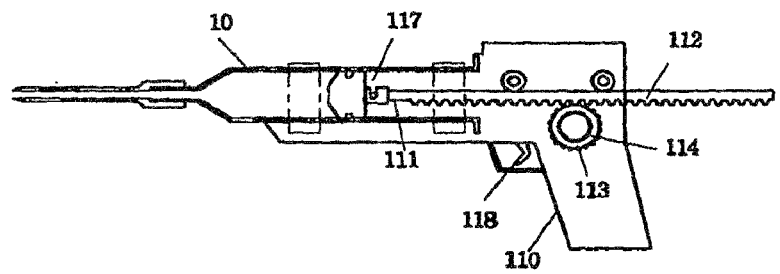
Figure 6:
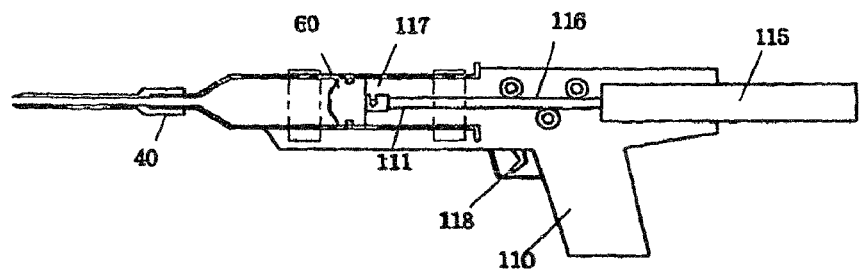
FIG. 6. schematic view of pneumatic cylinder as means for pressurization and decompression according to further embodiment of the present invention.

FIG. 5 and FIG. 6 illustrate a pressurization and decompression means having a structure to give mechanical pressure to the said piston head directly without using an air/suction pressure by means of pump. It is equipped with a gun-shaped holder 110 to fix detachably the FT receptacle, the said holder is joined with a shaft 111 reciprocating selectively. Under the state that the FT receptacle was joined with the holder, the said shaft can be joined detachably to the said piston head of the FT receptacle, therefore it is composed to give a negative/positive pressure selectively to the fat storing space.

FIG. 5 illustrates one embodiment of the said pressurization and decompression means, which is composed in order to move forward/backward selectively by a mechanic element comprising a rack 112 formed on the shaft, a pinion 113 formed on the holder, a motor 114 or rotate the said pinion. FIG. 6 illustrates another embodiment of that, which is composed of a structure connecting the shaft to an actuator 116 of a pneumatic cylinder 115 previously joined to the holder in order to move forward/backward selectively according to reciprocation of pneumatic cylinder.

The said embodiments of FIG. 5, 6 don't use air pressure as power source, but they are moved by electromotive force or pneumatic cylinder using the rotation of motor with hanging a detachable shaft on the piston head. The connecting parts of the shaft and the piston head are carried out in order to maintain a minimum connection transmitting a power without separation of both parts during reciprocation. And they are also carried out as a detachable structure in order to separate individually without difficulty.

Figure 7:
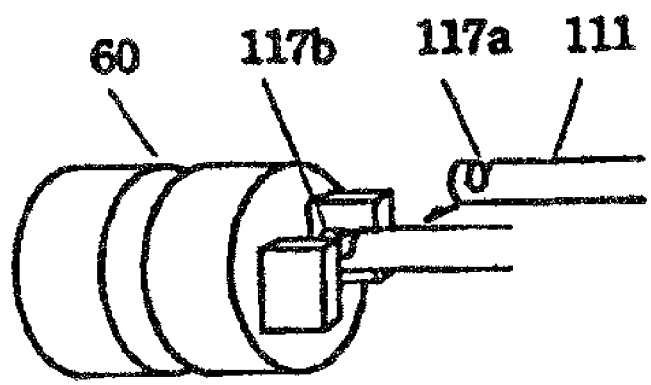
FIG. 7. schematic view of connecting parts of shaft to piston head according to further embodiment of the present invention FIG. 8. schematic view of stationary FT receptacle according to further embodiment of the present invention

Thereby the present invention is provided with a pin protruding on the piston head, a connecting parts 117 forming a U-shaped loop groove 117a on the one tip of the shaft to hang the piston head's pin to the said groove easily as shown in FIG. 7.

In according to the said composition, it is desired that a regulation switch 119 maintaining regular pressure should be attached in order to regulate and monitor motor's rotation speed, rotation force and not to move excessively the piston head forward or backward.

Moreover, it can be composed of a pressure sensor, which is attached to one end of the shaft joined to the piston head to control the motor's rotation or the pneumatic cylinder's movement. Thereby it is possible to regulate the piston's driving/backing power and speed using the switch to allow uses to see the position of the piston head with the naked eye.

Figure 8:
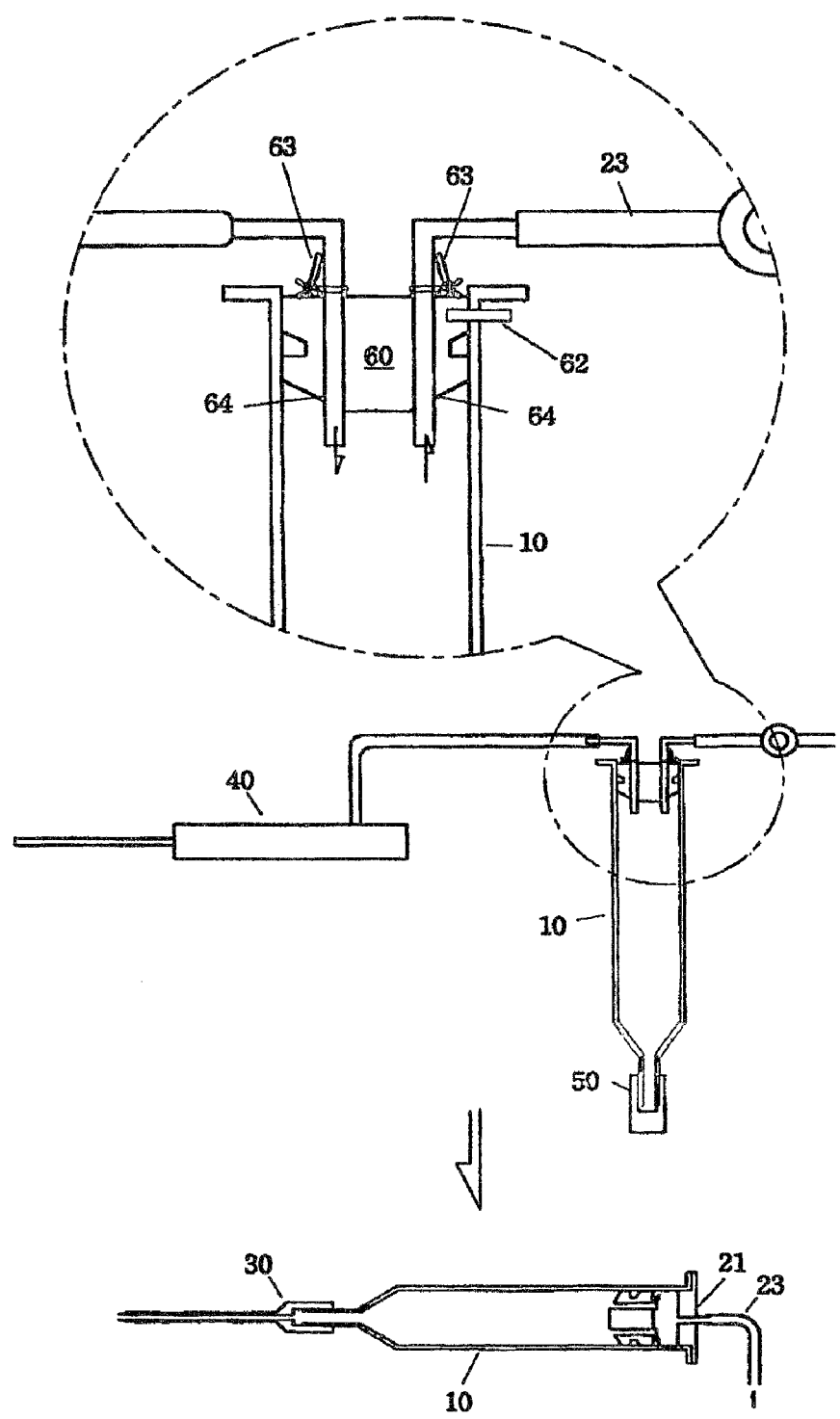

FIG. 8 illustrates an embodiment of a structure for simple air exhaust, which comprises a FT receptacle whose vertical hem portion joined with a stopple substituting for a syringe or cannulae, a piston head fixed on the rear tip of the FT receptacle by a locking pin 62, two penetration pipes 64 having a pressure interception valve individually, which are formed on the said piston head. The said penetration pipe 1 of the piston was joined to a cannulae, the other penetration pipe 2 was joined to external tube 23. If negative pressure is formed under the state the locking pin is fixed, fat is extracted. Thereafter, the cannulae and suction unit are separated under the state the locking pin is removed, thereby a pressure interception valve 63 closes the penetration pipes to keep airtight the fat storing space. Under that condition, a rear stopple 21 is included to keep airtight the rear pressurization and decompression space of the FT receptacle, wherein the said rear stopple forms connecting jack 22 to connect external tube and having a structure to be connected to external air pressure unit. Under the state syringe needle is attached to the vertical hem portion of the FT receptacle, fat transplantation is performed through the syringe needle giving air pressure to the rear space of the piston head.

The said example is free from an inconvenience that, if air flows in the front of the piston head during liposuction, it is necessary to stand the FT receptacle and to give a negative pressure again in order to exhaust the air. Finally, if the penetration pipes of the piston head are closed and locking is released, only air can be exhausted. Therefore it has no difficulty to remove air and it is profitable in surgery on the site where air inflows frequently.

Also, it is possible to separate liquid ingredients without centrifugation because it always maintains its position vertically. Therefore there is an effect to reduce the process.

The present invention according to above compositions can perform efficiently mass fat transplantation like a breast augmentation using the fat from liposuction, and it has a feature of using large capacity of FT receptacle for both aspiration and injection.

Moreover, other feature of the present invention is a mechanical or pneumatic pressurization and decompression means applied initially to fat transplantation system.

The present invention has further features that it can minimize air contact during liposuction in comparison with existing method, and it can inject directly aspirated fat without receptacle transfer. Therefore it can be applicable to mass fat transplantation (30 cc or more).

Further, the present invention can make mass fat transplantation safe and simple, so that the breast or hip augmentation surgery is realized easily. No matter how small transplantation, it can reduce remarkably air contact, thereby it is safe from infection.

What is more, since the present invention uses external power source, problem of injection resistance can be solved. It is possible to inject freely a fat into necessary site, so that cosmetic effect can be increased while at the same time much thinner needle can be utilized.

Injection resistance may cause a fat embolism once in a while. In case of hand-operated injection, pressurization is not regular and regulation/monitoring is difficult. However, in case of using external power source, fat embolism can be prevented due to easy regulation/monitoring. Thus it prevents fat embolism while at the same time it maximizes the fat survival rate due to pressure regulation. Also injection with regular pressure is possible perceiving and regulating the injected fat. Therefore even if needle injection speed is not regular, fat can be distributed equally. For example, if injection pressure is increased at a certain site, this means that the resistance increases, so to speak, this means the fat of the site is excessive. Accordingly the injection is stopped. If needle is moved other site, resistance is decreased in a moment and fat is pressurized and injected again. So equal fat distribution can be performed. It regulates not to generate excessive high pressure at a certain site, consequently it can prevent adipose cell from destruction as well as fat embolism caused by excessive fat inflow into blood vessel.

In addition, it simplifies surgical instruments, so usage is convenient. Since it utilizes air pressure dumped from suction unit during surgery, its equipment can be simplified and manufacture is also convenient. In other words, it can gain economical benefit to reduce a unit price.

Meanwhile, if electromotive is utilized as its pressurization and decompression means and power source instead of air pressure, it is feasible to perform liposuction and fat transplantation without large suction unit.

In virtue of these features, mass fat transplantation gets to be practicable, thereby application range can be extended. And the present invention is applicable to breast augmentation as the best embodiment.

Mostly silicone implant is utilized in existing breast augmentation method. It has many problems such as bad feeling, rupture possibility of rupture, danger at the time of rupture, possibility of infection in comparison with autologous tissue transplantation. But there is no practicable method for autoulogous tissue transplantation, almost methods using artificial implants have been utilized.

The present invention is also applicable to mass fat transplantation for hip-up.

In the great quantity of aspirated fat, only small quantity of fat is used and the rest is wasted at the time of liposuction for cosmetic purpose. The present invention takes advantage of waste fat to breast augmentation efficiently, thereby improving the value of liposuction.

INDUSTRIAL APPLICABILITY

1) It can reduce possibility of infection since it intercepts chance of contact with germs during fat transplantation.
2) It can reduce the operation time due to its simple process and short injection time using air pressure or power source.
3) Since it uses air pressure or power source, it is possible to form high injection pressure. Therefore no matter how strong the resistance of donor site, it can inject fat into necessary site freely.
4) Since free injection is feasible, it can distribute fat equally. In result, contact area of transplanted fat with body and survival rate can be increased.
5) Since mass fat transplantation is practicable, it can be utilized in surgeries, which need a large quantity of volume replacement such as breast augmentation.
6) Extraction receptacle is directly available as fat reservoir during liposuction, so that it is easy to refrigerate aspirated fat in aseptic condition.
7) Since it is mounted directly to a centrifuge without fat transfer, its process gets to be simplified and contamination possibility also gets to be reduced. Besides in some cases, centrifugation is omitted from its process, so that it becomes more simplified.
8) Fat has been collected in a small unit of 50-100 cc as compared with the existing 2000 cc-3000 cc of collection bottle. Therefore it can decrease possibility of dissymmetry, since it can perceive more accurately liposuction amount of each site.
9) Because it can utilize the existing disposable syringes, usage is economical and convenient. Also it utilizes them as disposables, ultimately the contamination possibility is minimized.
10) It is possible to use joining itself to reciprocating powered handpiece, therefore it can minimize the fat extraction time.
11) Using air pressure dumped from vacuum pump, it can perform two objects and manufacture power source for pressurization and decompression economically and simply.
12) Since it can perceive and regulate pressure precisely by machine as compared with hand-operated injection, it is feasible to inject fat at uniform density, it helps prevent fat embolism caused by high pressure injection, and it can prevent ruin of fat cell.

The invention claimed is:

1. A closed loop fat transplantation system comprising:
a fat transplantation receptacle (hereinafter referred as FT receptacle), wherein the FT receptacle includes a vertical hem portion which can join an individual syringe needle or a cannula selectively, a cylinder-shaped receptacle to aspirate and store a predetermined amount of fat, a piston head that is inserted to divide the cylinder-shaped receptacle into a front fat storing space and a rear pressurization and decompression space; and
an exterior mechanical pressurization and decompression means, wherein the pressurization and decompression means can apply positive/negative pressure to the rear pressurization and decompression space and has a structure separable from the FT receptacle, and wherein the mechanical pressurization and decompression means is a rear stopple to keep airtight the rear pressurization and decompression space of the FT receptacle, wherein a connecting jack is formed on the rear stopple to connect an external tube and then to connect an external suction unit or an air pressure unit, whereby applying positive/negative pressure to the rear pressurization and decompression space by replacing the external suction unit or the air pressure unit,
whereby fat transplantation can be performed without receptacle exchange using the same FT receptacle by extracting fat from a portion of a patient's body by applying negative pressure to the rear pressurization and decompression space, and transplanting fat to the other portion of the patient's body by applying positive pressure to the rear pressurization and decompression space,
wherein the closed loop fat transplantation system further comprises a front stopple; and a locking pin; and two penetration pipes, wherein the front stopple is joined with the vertical hem portion of the FT receptacle to replace the syringe or the cannula, wherein the locking pin fixes the piston head on a rear tip of the FT receptacle, wherein the two penetration pipes have a pressure interception valve individually, which are formed on the piston head, wherein one of the penetration pipe is connected to the cannula, wherein the other one of the penetration pipe is connected to the external suction unit; wherein when the locking pin is fixed and negative pressure is applied, fat is extracted; wherein when the cannula and the suction unit are separated from the FT receptacle and the locking pin is removed, the pressure interception valves close the penetration pipes to keep the fat storing space airtight; wherein when the locking pin is removed and the valves close the penetration pipes, the rear stopple is attached to the FT receptacle to keep the rear pressurization and decompression space of the FT receptacle airtight, wherein the connecting jack is formed on the rear stopple to connect an external tube so that the connecting jack is connected to an external air pressure unit; wherein when the syringe needle is attached to the vertical hem portion of the FT receptacle, fat transplantation is performed through the syringe needle by applying air pressure to the rear space of the piston head.

* * * * *